(12) United States Patent
Steffens et al.

(10) Patent No.: US 9,029,595 B1
(45) Date of Patent: May 12, 2015

(54) METHOD FOR WORKING UP DISTILLATION RESIDUES FROM ISOCYANATE PRODUCTION

(71) Applicant: Bayer MaterialScience LLC, Leverkusen (DE)

(72) Inventors: Friedhelm Steffens, Leverkusen (DE); Tim Loddenkemper, Dormagen (DE); Rainer Bellinghausen, Odenthal (DE); Hartwig Kempkes, Overath (DE)

(73) Assignee: Bayer MaterialScience AG, Leverkusen (DE)

( * ) Notice: Subject to any disclaimer, the term of this patent is extended or adjusted under 35 U.S.C. 154(b) by 0 days.

(21) Appl. No.: 14/413,095

(22) PCT Filed: Jul. 9, 2013

(86) PCT No.: PCT/EP2013/064444
§ 371 (c)(1),
(2) Date: Jan. 6, 2015

(87) PCT Pub. No.: WO2014/009342
PCT Pub. Date: Jan. 16, 2014

(30) Foreign Application Priority Data

Jul. 11, 2012 (EP) .................................. 12175958

(51) Int. Cl.
*C07C 263/20* (2006.01)
*C07C 263/10* (2006.01)
(52) U.S. Cl.
CPC ............. *C07C 263/20* (2013.01); *C07C 263/10* (2013.01)
(58) Field of Classification Search
None
See application file for complete search history.

(56) References Cited

U.S. PATENT DOCUMENTS

| 3,128,310 | A | | 4/1964 | Koch |
| 3,331,876 | A | | 7/1967 | Van Horn et al. |
| 3,544,611 | A | | 12/1970 | Michelet et al. |
| 4,216,063 | A | | 8/1980 | Ailloud et al. |
| 4,289,589 | A | * | 9/1981 | Koehler et al. ................ 203/49 |
| 4,918,220 | A | | 4/1990 | Collas et al. |
| 5,446,196 | A | | 8/1995 | Benedix et al. |
| 5,449,818 | A | | 9/1995 | Biskup et al. |
| 5,508,442 | A | | 4/1996 | Wagner et al. |
| 5,599,968 | A | | 2/1997 | Bankwitz et al. |
| 5,679,839 | A | | 10/1997 | Armand et al. |
| 5,931,579 | A | | 8/1999 | Gallus et al. |
| 6,443,170 | B1 | | 9/2002 | Vansant et al. |
| 6,803,438 | B1 | | 10/2004 | Brocchini et al. |
| 8,030,522 | B2 | | 10/2011 | Zechlin et al. |

(Continued)

FOREIGN PATENT DOCUMENTS

DE 270313 12/1911
WO 2014/009342 A1 1/2014

OTHER PUBLICATIONS

Chem System's PERP Report for TDI/MDI (Chem Systems, Process Evaluation Research Planning to TDI/MDI 98/99 S8, Tarrytown, N.Y., USA; Chem Systems 1999, p. 27 to 32.

(Continued)

*Primary Examiner* — Karl J Puttlitz
(74) *Attorney, Agent, or Firm* — Donald R. Palladino

(57) ABSTRACT

The present invention relates to a method for working up distillation, residues from isocyanate production in which monomeric isocyanate present in distillation residues is recovered by means of a spray-dry method and the overall yield of monomeric isocyanate is thus significantly increased.

9 Claims, 2 Drawing Sheets

(56) References Cited

U.S. PATENT DOCUMENTS

| | | |
|---|---|---|
| 8,063,241 B2 | 11/2011 | Lorenz et al. |
| 8,440,856 B2 | 5/2013 | Bock et al. |
| 8,692,016 B2 | 4/2014 | Sanders et al. |
| 2003/0230476 A1 | 12/2003 | Brady et al. |
| 2004/0118672 A1 | 6/2004 | Grun et al. |
| 2010/0010257 A1 | 1/2010 | Hansen et al. |

OTHER PUBLICATIONS

Ullmann's Encyclopedia of Industrial Chemistry, vol. 20, p. 63 et seq., Wiley VCH Verlags GmbH & Co. KGaA.
G. Oeriel (Ed,) Polyurethane Handbook, 2nd edition, Hanser Verlag, Munich, 1993, p. 60-84 et seq.
G. Wegnener et al. Applied Catalysis A: General 221 (2001). p. 303 to 335, Elsevier Science B.V.

* cited by examiner

*Figure 1a:*
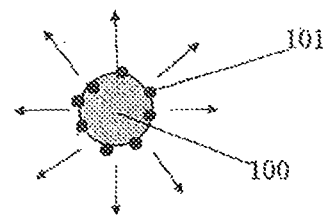
*Figure 1b:*
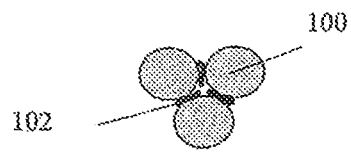
*Figure 1c:*
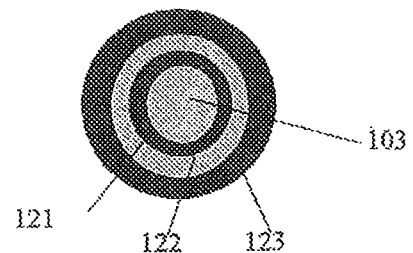
Fig. 1

METHOD FOR WORKING UP DISTILLATION RESIDUES FROM ISOCYANATE PRODUCTION

CROSS-REFERENCE TO RELATED APPLICATIONS

This application is a National Phase Application of PCT/EP2013/064444, filed Jul. 9, 2013 which claims priority to European Application No. 12175958.3, filed Jul. 11, 2013 each of which being incorporated herein by reference.

FIELD

The present invention relates to a process for working up distillation residues from isocyanate preparation, in which monomeric isocyanate present in distillation residues is recovered by means of a spray drying process and the total yield of monomeric isocyanate is increased significantly in this way.

BACKGROUND

In the industrial preparation of isocyanates, distillation residues are produced, which require further working up. These distillation residues comprise, inter alia, polymeric products and still contents of monomeric isocyanate. The present invention relates to a process which renders it possible to recover this content of monomeric isocyanate in the distillation residue in a high yield in a simple manner.

The state of the art for treatment of the said distillation residues of isocyanate preparation describes various processes. General aims of treatment of residues are maximizing of the isocyanate yield, minimizing of the amount of residue produced and an as appropriate as possible inexpensive and simple utilization of the amount of residue which is no longer usable for the isocyanate preparation process.

The following processes are chiefly known:

In principle, the distillation residue can be burned continuously or discontinuously. The process is technically simple and can be employed for generating service steam if a plant for thermal utilization which is suitable for this exists close to the isocyanate production plant, in order to ensure disposal via a pipeline connection. The great disadvantage of this process, however, is the loss in yield caused by the fact that the distillation residue always also comprises contents of the valuable product, which is burned at the same time. If the distillation of the isocyanate were to be operated such that the isocyanate were removed completely or almost completely from the bottom product, a solid residue which can be processed only with great difficulty would remain. To avoid this, the distillation conditions are conventionally chosen such that the bottom product of the distillation column remains liquid, which is only successful, however, if this still comprises a substantial content of the desired isocyanate, which is therefore inevitably co-fed to the combustion.

To minimize the losses in isocyanate yield, the distillation residue can be transferred into a stirred and heated tank and mixed with high-boiling hydrocarbons, preferably bitumen, which are inert under the distillation conditions, in order to distil off as completely as possible the free isocyanate still present in the residue (EP 0 548 685 A2). The residue which remains, which has been freed from isocyanate, can be discharged as a free-flowing solid and fed to a combustion. Disadvantages of this process are, in addition to the use of a substance foreign to the process (bitumen), losses in yield due to polymerization of the isocyanate, since the process includes long dwell times at a high temperature.

A further process for separating off the isocyanate residue is characterized by the use of kneader driers (EP 0 626 368 A1). In this process, the heated and stirred tanks described above are replaced by kneader driers. By employing, for example, bitumen, as in the abovementioned example the residue which remains is obtained as a free-flowing solid which can be employed as a fuel, for example in cement works. The advantage of this process over that mentioned above is an increase in yield, but the higher investment costs due to the more involved technique may be seen as a disadvantage. The use of mechanically moved parts moreover necessarily leads to a higher outlay on maintenance.

EP 0 699 659 A2 describes a process and a device for separating off a solid residue from a solution of the residue in vaporizable valuable substances and/or solvents with the addition of up to 20 wt. % of high-boiling hydrocarbons which are inert under the vaporization conditions of the valuable substances, heating of the mixture to the vaporization temperature in vacuo, whereupon the valuable substances vaporize and are stripped off and condensed and the residue is obtained as a free-flowing solid, the residue solution being introduced on to a stirred bed of granular, solid material kept at the vaporization temperature. A disadvantage here is the additional use of high-boiling solvents, which have to be worked up in a further process.

The patent literature also describes processes in which isocyanate distillation residues are reacted chemically in order to obtain industrially usable valuable substances, such as, for example, the reaction of residue from the preparation of toluylene-diisocyanate with alkanolamine (U.S. Pat. No. 5,902,459) or with isocyanates of the diphenylmethane series (DE 42 11 774 A1, U.S. Pat. No. 3,694,323).

The hydrolysis of isocyanate distillation residues with water for the purpose of recovery of the starting amine, in particular in the preparation of toluylene-diisocyanate (TDI in the following) is a field which has already been worked on for a relatively long time and is described, for example, in U.S. Pat. No. 3,128,310, U.S. Pat. No. 3,331,876, GB 795,639, DE 27 03 313 A1 and EP 1 935 877 A1. In the processes cited, isocyanate distillation residue is hydrolysed with water under increased pressure and at elevated temperature. In this context, some of the residue is converted into the original amine, which can be recycled into the phosgenation process again after appropriate working up and therefore leads to minimizing of the residue. The unsatisfactory part of this process is that some of the valuable product, isocyanate, is hydrolysed to the starting substance again, and must be phosgenated again. As a result, the isocyanate contained in the residue is indeed fed to an appropriate substance utilization, but it would be desirable to be able to recover the isocyanate as such from the residue.

EP 1 413 571 A1 and EP 1 371 633 A1 are concerned with optimizing the working up of TDI by employing a dividing wall column in the distillation, which results inter alia in a reduction of the content of TDI in the bottom product. Here also, however, production of an isocyanate-containing distillation residue cannot be prevented.

EP 0 017 972 A1 describes a process for separating off TDI and/or higher-boiling solvents from distillation residues which are formed in the preparation of TDI by phosgenation of toluylenediamine, by evaporation in a fluidized bed at temperatures of from 140 to 280° C. For this purpose, the distillation residue is heated up and is sprayed at temperatures of from 50 to 300° C. via an introduction device, for example a two-component nozzle or several one-component nozzles, into a fluidized bed of small initially introduced particles of particular particle sizes (0.5 to 5,000 µm) and a fluidizing gas. The initially introduced particles are residue which has already been worked up and is substantially free from the valuable substance (cf. for example p. 6, 1. 8 to 21 and p. 7, 1. 15 to 17 and 32 to 36). In this process, the drops of the distillation residue which are introduced into the fluidized container by means of the introduction device are sprayed on to the surface of the initially introduced particles and spread there, which leads to vaporization of the valuable product (TDI and/or higher-boiling solvent) and leads to the build-up of shell-like granules of residue which is free from the valuable substance. The vaporization of the valuable product takes place on the initially introduced particles. The residue to be worked up is already depleted in isocyanate before introduction into the fluidized reactor to the extent that it must be injected into the fluidized bed at least partly as a melt (p. 4, 1. 20 to 23), since too high a viscosity impedes the atomization process. A disadvantage is that the particle size of the initially introduced particles must be established in an involved manner (cf. for example the guiding of the particles in the figure via the discharge (5), the "grading device" (18) and the comminuting device (8) back into the fluidized reactor).

Such a granulation process as a rule does not have relatively long cycle times and must be shut down after certain intervals of time for the purpose of intermediate cleaning. For the present case of working up of isocyanate-containing residues this is a disadvantage due to the required inertization of the reaction space and the high temperatures as well as the start-up problems. A stationary process requires that a bed having a specific particle size distribution is established again in the fluidized bed. For example, if a fine content is lacking, there is the danger that the reactor runs empty after the original bed content has grown, while if the fine content is too high, the formation of too large a bed can take place and the process can collapse as a result of the high mechanical wear which then occurs. Such granulation processes are therefore usually closely observed by regular sampling and/or visual observation possibilities. Both measures not only require an increased outlay on manual supervision, but also are more difficult to realize due to the process conditions required, in particular due to the inertization and high temperatures already mentioned above.

As a result of the abovementioned disadvantages of the state of the art, there was a demand for a simple and economical process for the production of monomeric isocyanate from a distillation residue produced in isocyanate preparation. This should be distinguished in particular by operating stability with a minimized outlay on supervision, in addition to the highest possible yield of monomeric isocyanate.

SUMMARY

Taking into account this demand, the present invention provides a process for the preparation of an isocyanate, comprising the following steps:
  a) phosgenation of a primary amine to obtain a crude process product comprising the corresponding isocyanate,
  b) working up of the crude process product obtained under a), wherein the working up comprises at least one distillation step in which monomeric isocyanate, as the distillate, and a distillation residue (100) comprising, in addition to non-vaporizable contents, such as, for example, polymeric isocyanate species, monomeric isocyanate are obtained,
  c) working up of the distillation residue (100) obtained under b), wherein the distillation residue (100) and a carrier gas (110) are sprayed into a reactor (1), the distillation residue (100) and the carrier gas (110) flowing vertically downwards, so that the monomeric isocyanate vaporizes partly to completely and a dried residue (120) which has been largely to completely freed from monomeric isocyanate and a stream (130) comprising monomeric isocyanate are obtained in this way.

The process according to the invention is a so-called spray drying process. In contrast to granulation drying processes (EP 0 017 972 A1), here the distillation residue (100) obtained in step b) is not sprayed into a fluidized bed on entry into the reactor (1). If a fluidized bed is employed at all in the process according to the invention, this is passed through only after a significant predrying of the residue and removal of the stream (130) comprising monomeric isocyanate, which has the advantages described in detail below.

BRIEF DESCRIPTION OF THE DRAWINGS

FIG. 1*a* (according to the invention) shows a diagram of a drying residue particle 100 which is covered by release agent particles 101.

FIG. 1*b* (according to the invention) shows a diagram of a low-dust agglomerate which is obtained when the predried residue is led through a fluidized bed of solid particles 102.

FIG. 1*c* (not according to the invention, drying by means of granulation) shows a diagram of the onion-shaped construction of a residue particle dried by means of granulation.

DETAILED DESCRIPTION

Figure 2:
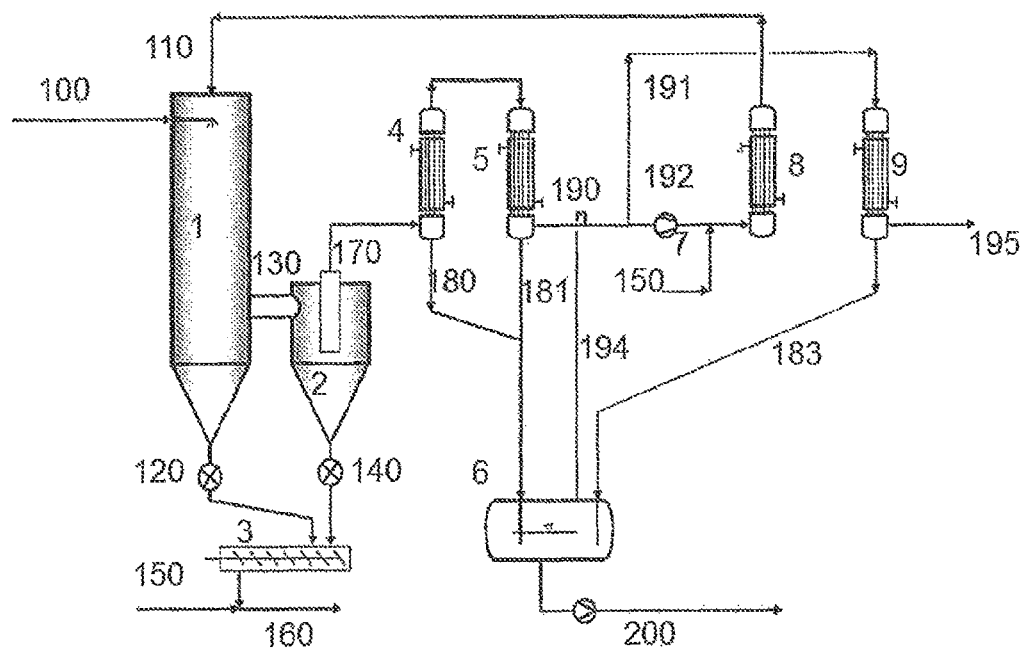
FIG. 2 illustrates an embodiment of the process according to the invention.

The invention is explained in detail in the following. In this context, various embodiments can be combined with one another as desired, if the opposite does not clearly emerge from the context.

Suitable primary amines for carrying out step a) of the process according to the invention are, in particular, the isomers of toluylenediamine (TDA in the following), the isomers of naphthyldiamine (NDA in the following), 1,6-hexamethylenediamine (HDA in the following), the isomers of isophoronediamine (IDPA in the following) and the isomers of diaminodicyclohexylmethane (H12-MDA in the following). TDA is particularly preferred, the precise isomer composition present in each case being irrelevant for the process according to the invention. TDA, which is preferably employed, conventionally comprises 78% by weight to 82% by weight of 2,4-TDA and 18% by weight to 22% by weight of 2,6-TDA, based on the total weight of the 2,4- and 2,6-TDA isomers. Based on the total weight of the TDA, in this context the 2,4- and 2,6-TDA isomers preferably make up in total from 95.0% by weight to 100% by weight, particularly preferably from 98.0% by weight to 100% by weight. The phosgenation of such a primary amine to give the corresponding isocyanate is known in principle and can be carried out by any of the processes known in the state of the art. The processes described in the following literature passages may be mentioned as examples: Ullmann's Encyclopedia of Industrial Chemistry, Vol 20, p. 63 et seq, Wiley VCH Verlags GmbH and Co., KGaA, Weinheim, G. Oertel (Ed.) Polyurethane Handbook, 2nd edition, Hanser Verag, Munich, 1993, p. 60 et seq., G. Wegner et al. Applied Catalysis A: General 221 (2001), p. 303 to 335, Elsevier Science B.V., EP 1369 412 A1, EP 1 754 698 B1 and EP 0 289 840B1.

The reaction of primary amine and phosgene in step a) preferably takes place as follows:

Phosgene is employed in a stoichiometric excess, based on the primary amine. The phosgenation can be carried out in the liquid and in the gas phase. A procedure between these two extremes ("aerosol phosgenation") is also conceivable. In all process variants a solvent is employed, either in order to dissolve the starting substances therein (liquid phase phosgenation) or, in the vaporized state, as an inert additive or as a reaction interruption medium in the so-called "quench" (gas phase phosgenation). Preferred solvents are chlorinated aromatic hydrocarbons, such as, for example, chlorobenzene, o-dichlorobenzene, p-dichlorobenzene, trichlorobenzenes, the corresponding chlorotoluenes or chloroxylenes, chloroethylbenzene, monochlorodiphenyl, α- and β-naphthyl chloride, benzoic acid ethyl ester, phthalic acid dialkyl esters, diethyl isophthalate, toluene and xylenes. Further examples of suitable solvents are known from the state of the art. As is furthermore known from the state of the art, e.g. WO-A-96/16028, equally the isocyanate formed can itself function as a solvent for phosgene. Particularly preferred solvents are chlorobenzene and dichlorobenzene, and o-dichlorobenzene is exceptionally particularly preferred.

Examples of liquid phase phosgenations are described in DE 37 44 001 CI, EP 0 314 985 A1, EP 1369 412 A1 and the literature cited there.

Examples of gas phase phosgenations are described in EP 0 570 799 A1, EP 1 555 258 A1, EP 1 526 129 A1 and DE 101 61 384 A1, and in particular for aliphatic isocyanates in EP 0 289 840 B1 and EP 1 754 698 B1. Advantages of this process over the otherwise conventional liquid phase phosgenation lie in the saving of energy due to minimizing of an involved solvent and phosgene circulation.

The primary amine can be reacted with phosgene in a one-stage or two-stage or optionally multi-stage reaction. In this context, a continuous and also a discontinuous operating procedure is possible.

If a one-stage phosgenation in the gas phase is chosen, the reaction is carried out above the boiling temperature of the primary amine, preferably within an average contact time of from 0.05 to 5 seconds and at temperatures of from 200° C. to 600° C. (see DE 101 61 384 A1).

In the phosgenation in the liquid phase, temperatures of from 20° C. to 240° C. and absolute pressures of from 1 bar to 50 bar are preferably employed (see U.S. Pat. No. 3,544,611).

In step a), independently of the precise procedure, a crude process product comprising the corresponding isocyanate is obtained. In this context, the isocyanate product is conventionally obtained as a mixture of monomeric and polymeric species. In the context of this invention, monomeric isocyanate is understood as meaning the simplest isocyanate of a homologous series. In the case of TDA as the starting amine, this corresponds to toluylene-diisocyanate (TDI in the following), in the case of NDA naphthyl-diisocyanate (NDI in the following), in the case of HDA 1,6-hexamethylene-diisocyanate (HDI in the following), in the case of IDPA isophorone-diisocyanate (IDPI in the following) and in the case of H12-MDA diisocyanatodicyclohexylmethane (H12-MDI in the following). If the starting amine is a mixture of various isomers, the isomer distribution of the corresponding isocyanate substantially corresponds to that of the starting amine.

In addition, in the phosgenation of a primary amine polymeric isocyanate species, the structure of which is not always known exactly, are conventionally also formed. These are conventionally higher molecular weight species which can be derived formally from polymerization products of the amine employed by replacement of the amine groups by isocyanate groups. It is known e.g. that at higher temperatures TDI tends towards dimerization (or polymerization) with splitting off of $CO_2$. Such and similar processes give rise to the formation of polymeric isocyanate species. These polymeric isocyanate species can partly also additionally form in step b).

After the phosgenation in step a), the working up of this crude process product is carried out in step b). This is preferably effected by first separating the crude process product from step a) into a liquid and a gaseous product stream in a manner known to the person skilled in the art. The liquid product stream, the crude isocyanate, substantially comprises isocyanate as a mixture of monomeric and polymeric species, the solvent and a small content of unreacted phosgene. The gaseous product stream substantially comprises hydrogen chloride gas, stoichiometrically excess phosgene, further gases, such as, for example, nitrogen and carbon monoxide, and slight amounts of solvent. This gaseous product stream is fed to a further working up, where as a rule solvent, excess phosgene and the hydrogen chloride gas formed are separated off. Solvent and excess phosgene are fed back to the reaction for economic reasons. The hydrogen chloride can be fed to various possible uses, such as, for example, an oxychlorination of ethylene to give ethylene dichloride or a recycling process, which recycles chlorine into the isocyanate process again. These recycling processes include the catalytic oxidation of hydrogen chloride, e.g. by the Deacon process, the electrolysis of gaseous hydrogen chloride and the electrolysis of an aqueous solution of hydrogen chloride (hydrochloric acid).

The liquid product stream, the crude isocyanate, is then fed to an in general multi-stage working up by distillation, dissolved phosgene and the solvent being separated off. This working up of the crude isocyanate by distillation can be carried out by generally known methods. Examples are described in EP-A-1 413 571, US 2003/0230476 A1 (TDI), and EP 0289 840 B1 (HDI, IDPI and H12-MDI).

The working up by distillation of the TDI particularly preferably prepared by the process according to the invention is preferably carried out by one of the three variants described in the following:

Variant 1

Variant 1 is described in principle in Chem System's PERP Report for TDI/MDI (Chem Systems, Process Evaluation Research Planning TDI/MDI 98/99 S8, Tarrytown, N.Y., USA: Chem Systems 1999, p. 27 to 32). In this, the liquid reaction mixture still comprises a solvent content of >50 wt. %, preferably 55 wt. % to 65 wt. %, after the phosgene has been separated off by distillation. This mixture is fed to the separating off of solvent, wherein in a pre-evaporator a solvent/TDI mixture is distilled off in a solvent distillation column and a liquid bottom discharge of the pre-evaporator is fed to further processing, the so-called working up of the residue. This liquid stream comprises, in addition to 2 wt. % to 10 wt. % of solvent, approx. 5 wt. % to 20 wt. % of distillation residue. In the solvent distillation column solvent is distilled off and fed to the process again. This distillation can be carried out in one or two stages (U.S. Pat. No. 6,803,438 B2). The bottom product of this solvent distillation still comprises, in addition to TDI, 15 wt. % to 25 wt. % of solvent content. This stream is passed into a so-called refining column in which residual solvent is distilled off, and the solvent-free bottom product is fed to a purifying column which is operated under reduced pressure and delivers the purified sellable isocyanate TDI as the distillate. A residue-containing part stream from the column bottom of the purifying column is likewise fed to the separating off of residue. Alternatively, the tasks of the refining and purifying distillation columns can be combined here, as described in US 2003/0230476 A1, into a dividing wall column, a stream of low-boiling substances and solvent, a fraction of pure TDI and a product stream, as the bottom product, comprising TDI and higher-boiling components being obtained. The product stream mentioned last is in turn fed to a working up of the distillation residue. The working up of distillation residues described in Chem System's PERP Report for TDI/MDI (Chem Systems, Process Evaluation Research Planning TDI/MDI 98/99 S8, Tarrytown, N.Y., USA: Chem Systems 1999, p. 27 to 32 can be excellently replaced by step c) of the present invention.

Variant 2

In contrast to variant 1, in this embodiment the liquid reaction mixture still comprises a solvent content of <50 wt. % after the phosgene has been separated off by distillation. This mixture is fed to a pre-evaporator, from which a solvent/isocyanate mixture having a solvent content of <50 wt. % is distilled off in a distillation column, preferably over the top. This distillation column corresponds to the refining column in variant 1. The liquid bottom discharge of the pre-evaporator is fed to a further processing, the so-called working up of the residue. This liquid stream comprises, in addition to 2 wt. % to 10 wt. % of solvent, approx. 5 wt. % to 20 wt. % of distillation residue. The solvent-free bottom product of the refining column is passed into the purifying column, which is operated under reduced pressure and delivers the purified sellable isocyanate TDI as the distillate. A residue-containing part stream from the column bottom of the purifying column is likewise fed to the separating off of residue. Alternatively, the tasks of these refining and purifying distillation columns can be combined here, as described in EP 1 413 571 A1, into a dividing wall column, a stream of low-boiling substances and solvent, a fraction of pure TDI and a product stream, as the bottom product, comprising TDI and higher-boiling components being obtained. The product stream mentioned last is in turn fed to a working up of the distillation residue. In variant 2 also, the working up of the distillation residue can be excellently carried out according to step c) of the present invention.

Variant 3

Variant 3 comprises the distillation sequences described in variants 2 and 1, but without the pre-evaporator mentioned in each case, which feeds a liquid bottom discharge comprising approx. 5 wt. % to 20 wt. % of distillation residue to a working up of residue. In this case the content of distillation residue is co-fed in the distillation sequences described via the liquid quantitative streams up to the particular last TDI purification column. This process is likewise known in principle (EP 1 717 223 A2). In this case the distillation residue (mixture comprising toluylene-diisocyanate and distillation residue) is discharged completely to the working up of residue from the last distillation column. In variant 3 also, the working up of the distillation residue can be excellently carried out according to step c) of the present invention.

All the known processes for purification of the crude isocyanate by distillation in step b) have the common feature that in addition to the desired purified monomeric isocyanate from the distillation, a bottom product which still comprises monomeric isocyanate, that is to say valuable product, is obtained. This bottom product can be fed to the working up of residue according to the invention in step c) either directly (i.e. the distillation residue (100) is identical to the bottom product) or preferably after concentration in a suitable pre-drying apparatus. In the concentration step, a gas phase comprising monomeric isocyanate and, as a liquid phase, the distillation residue (100) which likewise still comprises monomeric isocyanate are obtained. Suitable pre-drying apparatuses are thin film evaporators, climbing film evaporators, falling film evaporators, long tube evaporators, helical tube evaporators, forced circulation flash evaporators and paddle driers or a combination of these apparatuses. A paddle drier is preferred, particularly preferably a paddle drier without a cooling zone and with a discharge screw for the distillation residue (100). The optional concentration in a predrying apparatus is earned out only to the extent that the distillation residue (100) which remains still stays flowable. In spite of this concentration step, it therefore still comprises substantial amounts of monomeric isocyanate.

The working up of this distillation residue 100 comprising, in addition to non-vaporizable contents, such as, for example, polymeric isocyanate species, monomeric isocyanate is the subject matter of step c) of the process according to the invention. In this step, the distillation residue (100) obtained in step b) is sprayed together with a carrier gas (110) into a reactor, the distillation residue (100) and the carrier gas (110) flowing vertically downwards, so that the monomeric isocyanate vaporizes partly to completely and a dried residue (120) which has been largely to completely freed from monomeric isocyanate and a stream (130) comprising monomeric isocyanate are obtained in this way. Suitable carrier gases in this context are those which, under the conditions present, do not react with the monomeric isocyanate to be separated off, that is to say are inert. Nitrogen, noble gases (such as Ar, He among others) and carbon dioxide are preferred. Nitrogen is particularly preferred, since it is sufficiently inert and inexpensive. It is also possible in principle, although not preferred, to use vapours of inert solvents (preferably chosen from chlorobenzene, ortho-dichlorobenzene, toluene, methylene chloride, chloroform, cyclohexane, hexane, xylene, isooctane, acetone, tetrahydrofuran, dioxane or mixtures of the abovementioned solvents, chlorobenzene and ortho-dichlorobenzene being particularly preferred) as the carrier gas.

Possible reactors in step c) are so-called spray towers which are known in principle from the state of the art. These are described, for example, in *Kroll: Trocknungstechnik 2nd volume, 2nd edition,* 1978, page 275-313, are conventionally cylindrical in construction and can have a diameter of from 2 m to 10 m with a height of from 5 m to 30 m. However, dimensions which deviate from these are also conceivable. Preferably, the reactor employed has a conical taper at the lower end (where the distillation residue depleted in monomeric isocyanate is sluiced out).

The distillation residue can be sprayed into the reactor with conventional atomizer units, such as, for example, pressure nozzles, one- or two-component nozzles or rotary atomizers. Preferably, spraying is carried out such that drop sizes in a suitable size distribution are formed which meet the quality requirements and can dwell in the spray tower long enough for complete evaporation of solvent residues to be achieved. The hot carrier gas, which provides the heat required for this, is fed in various ways depending on the atomizing unit used:

a) In the case of nozzles the carrier gas is fed via perforated trays in order to achieve a uniform distribution of the gas. If appropriate, the distribution of the hot gas can be improved further or adapted by angular momentum generated via a baffle plate or via a decentral inlet on the circumference of the cylindrical reactor.

b) If rotary atomizers are employed, the hot carrier gas is fed centrally via an annular gap above the atomizer and the distribution of the gas, like the distribution of the drops also, is established in the tower by adaptation of the angular momentum on the hot air paddles. Since the gas speeds with homogeneous distribution of the gas over the tower cross-section are very low, preferably 0.1 m/s to 1 m/s, particularly preferably 0.2 m/s to 0.5 m/s, and the drops emerge from the atomizers at significantly higher speeds (preferably 20 m/s to 200 m/s), the distribution of the gas and the distribution of the spray drops are to be matched to one another as described above.

In this manner, the distillation residue is sprayed into the reactor in the form of fine droplets. The average droplet diameter in this context is preferably from 1 µm to 500 µm, particularly preferably 20 µm to 300 µm. The spray drops are established such that an as complete as possible vaporization of the monomeric isocyanate is achieved in the reactor. Laboratory experiments with a cylindrical reactor (spray tower) having a conical taper at the lower end have shown that adequate drying is achieved with drops having an average diameter of 20 μm and a height of the cylindrical part of the reactor of 1 m height and 0.8 m cone length and a 0.8 m diameter of the cylindrical part of the reactor. On the production scale with reactors typically 10 to 30 m long, larger drops having an average diameter of from about 100 to 300 μm can also be dried.

The temperature of the distillation residue when sprayed into the reactor must be at least high enough for the viscosity of the residue to be low enough to be able to carry out an atomization. For this, from experience, the viscosity must be below 1,000 mPas, preferably below 300 mPas and particularly preferably below 100 mPas. Further information on the viscosity follows below. The temperature of the residue when sprayed into the reactor furthermore should be below the boiling temperature of the monomeric isocyanate, in order to prevent vaporization before or during the atomization. Flash vaporizations after or during the atomization can indeed shorten the drying times, but can also have the effect of a solidification of the drops before the formation of drops and thereby impede the atomization operation. The temperature of the distillation residue when sprayed into the reactor is therefore preferably established at a value of from 20° C. to 300° C., particularly preferably from 50° C. to 200° C., exceptionally particularly preferably from 80° C. to 180° C., and the temperature of the carrier gas when sprayed into the reactor is preferably established at a value of from 150° C. to 500° C., particularly preferably from 180° C. to 350° C., exceptionally particularly preferably from 220° C. to 280° C., depending on the temperature chosen for the temperature of the distillation residue when sprayed into the reactor. The distillation residue can be sprayed the most advantageously under these conditions.

As mentioned above, nozzle or rotary atomizers can be employed for the atomization. To achieve low-dust residues, pressure nozzles in which the distillation residue (100) to be atomized should have an absolute pressure of from 1.0 bar to 300 bar, preferably from 3.0 bar to 100 bar, particularly preferably from 5.0 bar to 20 bar are preferably employed. In the case of two-component nozzles and also in the case of rotary atomizers, a relatively high fine grain content must often be accepted. Furthermore, injection of release agents (see below) around the spray drops is also more difficult. For these reasons, pressure nozzles are particularly preferred. Suitable pressure nozzles are known per se to the person skilled in the art and are described, for example, in *Kroll: Trocknungstechnik, 2nd volume, 2nd edition,* 1978, page 282-288.

Preferably, when sprayed into the reactor at the particular temperature the distillation residue has a viscosity of from 1 mPa·s to 1,000 mPa·s, particularly preferably from 1 mPa·s to 300 mPa·s. In this context, the viscosity values obtained with a rheometer with double gap geometry (DG24/27) at 25° C. in the shear rate range of from 1 to 100 $s^{-1}$, standard: 90 $s^{-1}$ are determinative. After the measuring geometry has been filled with the sample, the measurements are started after an equilibration time of 120 s. 22 measurement points are recorded in the shear rate range of from 1 to 100 $s^{-1}$ in logarithmic distribution with a constant measurement point duration of 10 s. The use of a Bohlin CVO rheometer is preferred. If required, this viscosity is established by increasing the temperature in the abovementioned limits and/or by mixing the distillation residue with solvent, preferably process solvent (i.e. the same solvent as in step a)), or monomeric isocyanate. If monomeric isocyanate is employed for the dilution, the monomeric isocyanate recovered in the lateral take-off of the reactor is regularly higher than the use thereof for dilution of the distillation residue, so that overall the yield of monomeric isocyanate can be increased. Preferably, however, the distillation conditions in step b) are to be chosen such that the distillation residue already leaves the distillation column with the desired viscosity.

The drops of the distillation residue are dried by vaporization of the monomeric isocyanate. In this context, tacky, oligomeric constituents of the original distillation residue are polymerized completely so that overall a solid, free-flowing residue remains, which can be sluiced out of the reactor at its lower end.

In a preferred embodiment, the stream 130 comprising the monomeric isocyanate is sluiced out in a lateral take-off of the reactor 1 and the residue 120 is sluiced out of the reactor 1 below this lateral take-off. It is furthermore preferable here for the stream 130 sluiced out to be freed from fine dust in a separator (e.g. a cyclone). Compared with sluicing out of the reactor 1, at the bottom, of the residue 120 and the stream 130 comprising monomeric isocyanate together, with subsequent separation of these streams in a separator (e.g. cyclone or filter), which is also possible in principle, this procedure has the advantage that in the downstream separator an additional solid discharge of as a rule finer material is obtained, which can optionally be fed back as release agent into the tower (reactor 1), see below for further details.

In a preferred embodiment a release agent is added in order to facilitate the formation of non-tacky dried residue particles. Such release agents can be additives which are non-tacky at the temperature in the reactor, that is to say do not stick together into larger agglomerates when they collide, do not react with the isocyanate and do not impede the polymerization reaction of the oligomeric constituents of the original distillation residue. Preferably, the release agent is chosen from the group consisting of talc, chalk, inorganic pigments and completely polymerized residue. Among the inorganic pigments, titanium dioxide, iron oxides, aluminium oxide and other metal oxides are preferred in particular. Completely polymerized residue means the dried content of the original distillation residue. This can be obtained, for example, from dust separators (cyclones, filters, see below) or by grinding the residue discharged at the lower end of the reactor. The release agent either is mixed with the liquid distillation residue before introduction thereof into the reactor, or is introduced directly at the upper end of the reactor via a feed line, which is attached alongside the feed line of the distillation residue, into the reactor, where it enters directly into the drop stream and coalesces with this or settles on the surface of the predried drops. In both cases the release agent is introduced into the reactor together with or in the immediate vicinity of the distillation residue and is intended to prevent an agglomeration of the spray particles, in contrast to granulation processes in which solid particles are initially introduced into a fluidized bed in the reactor before the distillation residue is introduced, so that the distillation residue injected in precipitates on these solid particles and larger particles grow.

In a further preferred embodiment, in the variant with removal of the stream 130 in the lateral take-off the formation of non-tacky dried residue particles is facilitated in that after the monomeric isocyanate has been taken off in the lateral take-off the residue falling downwards is led through a fluidized bed, before it is sluiced out of the reactor 1 at the bottom. When it meets the fluidized bed, the residue has already been largely predried, i.e. preferably 50% to 99% of the monomeric isocyanate introduced into the reactor 1 with the distillation residue 100 has already vaporized and has been removed from the reactor 1 via the lateral take-off 130. The dimensions of the reactor 1, the temperature of the carrier gas 110 and that of the distillation residue 100 when sprayed into the reactor and the flow rates are preferably matched to one another in this embodiment such that the values of vaporized monomeric isocyanate mentioned are achieved.

The fluidized bed is preferably formed from the same solids, including the solid called a release agent above, and the same gas which is employed as the carrier gas (110). The carrier gas for the fluidized bed (also called fluidizing gas in the following) is fed into the reactor from the bottom, below the fluidized bed, and fluidizes the predried particles. As a result, a longer dwell time is achieved for complete drying and polymerization of the distillation residue. Due to the fact that in the process according to the invention the distillation residue is already largely predried on entry into the fluidized bed and the fluidized bed is arranged below the lateral take-off for the monomeric isocyanate (130), the residue particles do not form into onion-shaped granules by spreading of still liquid residue, but merely form into agglomerates by individual particles sticking together and lower-dust powders are thereby formed from thoroughly dried residue. This agglomeration is not absolutely necessary for the process, since the particles entering into the fluidized bed are already of an order of size with which a fluidized bed can be operated and are not discharged, or are discharged to only a small extent, with the fluidizing gas. If appropriate, the agglomeration must be limited by addition of release agents, so that no agglomerates which are too large, which are deposited on the inflow trays of the fluidized bed, are formed. The differences between the drying processes are shown in diagram form in FIG. 1:

FIG. 1a (according to the invention) shows a diagram of a drying residue particle 100 which is covered by release agent particles 101 which prevent or at least suppress a sticking together. The vaporization of volatile constituents is symbolized by the arrows.

FIG. 1b (according to the invention) shows a diagram of a low-dust agglomerate which is obtained when the predried residue is led through a fluidized bed of solid particles 102.

FIG. 1c (not according to the invention, drying by means of granulation) shows a diagram of the onion-shaped construction of a residue particle dried by means of granulation. In the core there is a solid particle 103 which was initially introduced into a fluidized bed into which the not yet predried residue was sprayed. These solid particles often comprise completely polymerized residue. Around the core are onion-shaped layers 121, 122, 123 etc. of dried residue.

In the process according to the invention, the solidified distillation residue 120 which has been largely to completely freed from monomeric isocyanate is sluiced out at the lower end of the reactor, which is preferably conical, through suitable discharge devices known per se to the person skilled in the art. Such discharge devices are preferably cellular wheel sluices. In the case of the embodiment with an attached fluidized bed at the base of the spray tower, the residue is removed laterally via a weir.

The monomeric isocyanate which has been separated off preferably leaves the reactor via a lateral take-off together with the majority of the carrier gas stream. In the less preferred embodiment of discharge of the residue and monomeric isocyanate together from the reactor 1, all the gas streams (carrier gas and vaporized monomeric isocyanate) and the residue particles are discharged together from the reactor at the bottom via a cone and are then separated from one another into the streams 120 and 130 in a separator (cyclone or filter). Further working up of these streams is then carried out in the same way as in the preferred embodiment of removal of stream 130 in a lateral take-off.

To separate out any entrained solid particles, the stream of monomeric isocyanate and carrier gas (130) is preferably passed through a cyclone or filter. The solid contents separated off there either are mixed with the residue 120 and further processed together, or they are employed as the release agent, as described above. The stream of monomeric isocyanate and carrier gas is now cooled as rapidly as possible in order to prevent a polymerization of the monomeric isocyanate. This is preferably effected by one or more heat exchangers in which the temperature of the gas stream is cooled from a temperature of from 150° C. to 250° C. (exit temperature on leaving the reactor) to a value of from 50° C. to 100° C. In addition to the cooling in a heat exchanger, it is also possible to cool the stream of carrier gas and monomeric isocyanate by injection of an inert solvent or by passing into an inert solvent. In this context, the same solvent as in step a) is preferably employed.

The monomeric isocyanate which has condensed out in this manner is preferably combined in part to completely, preferably completely, with the monomeric isocyanate obtained as the distillate in step b) and fed to further use. If the monomeric isocyanate obtained in step c) still comprises solvent (added, if appropriate, to establish a suitable viscosity or for cooling), this can of course be separated off beforehand.

The dwell time of monomeric isocyanate from entry into the reactor of step c) to cooling after leaving the reactor is preferably from 1 s to 100 s, particularly preferably from 3 s to 60 s and exceptionally particularly preferably from 10 s to 30 s. The desired dwell time in this context is matched to the dwell time required for vaporization of the monomeric isocyanate, in particular to the maximum dwell time required for the drops with the larger diameters. This dwell time is realized by the choice/design of the reactor length, matched with the gas speeds and sinking speeds of the drops. The lower the temperature and the shorter the dwell time, the lower the risk of a polymerization of the monomeric isocyanate. On the other hand, a certain minimum temperature and minimum dwell time are of course necessary for an as complete as possible vaporization of the monomeric isocyanate from the distillation residue, so that the parameters actually established reflect a compromise between these two requirements. One advantage of the present process is to be seen in that due to the evaporative cooling, the spray drops have a significantly lower temperature than the carrier gas surrounding them, as a result of which the tendency towards polymerization is suppressed further.

The gas phase which is obtained during the condensation of the monomeric isocyanate and substantially comprises the carrier gas is preferably recycled into the drying process via a circulating gas fan and after heating up to the desired reactor entry temperature. Furthermore, before the heating up and recycling, a part of the carrier gas recovered is sluiced out and if appropriate replaced by fresh carrier gas, in order to sluice non-condensable gases which may form during the vaporization and partial polymerization out of the process and in order to avoid, where appropriate, a concentration of components which cause trouble in a larger amount (e.g. gas contents in the residue or from decomposition/polymerization reactions, dedusting gas from the filter dedusting, infiltrated air, e.g. from cellular wheel sluices). The removal of this small waste gas stream from the process is preferably carried out after the circulating gas fan, in order to utilize the pressure build-up during the ventilation and to be able to implement the small waste gas stream without further transport/pressure build-up units (ventilator, injector or the like). To increase the availability of the process, in a preferred embodiment so-called CIP (CleanInPlace) cleaning systems are recommended in all units, which, by targeted local injection of cleaning liquid and collection of the cleaning liquid via closable outlets and a collecting tank, from which the pump for spraying is fed, allows on-site cleaning of the units without neutralization of the inertization and manual opening of the apparatuses. Use can already be made of this principle in the condenser, in that it is configured as a washer and solvent is sprayed.

FIG. 2 illustrates a possible embodiment of the process according to the invention by the example of a distillation residue 100 which is to be worked up, which originates from a TDI production plant and comprises 50% by weight, based on the total weight of 100, of monomeric TDI:

The distillation residue 100 to be worked up, with a temperature of 150° C., is introduced at 2,000 kg/h into the spray tower 1 at the upper end of this, as is the carrier gas 110, which has a temperature of 300° C. and is under an absolute pressure of 1,200 mbar. The completely polymerized residue leaves the spray tower 1 at the lower end of the cone as stream 120 with a temperature of 250° C. The monomeric isocyanate (TDI) is contained in the lateral take-off stream 130. This is freed from entrained dust contents in a cyclone 2. These are discharged as stream 140 and cooled together with 120 in a cooling screw 3. The discharge from the cooling screw is charged with nitrogen (150) and fed as stream 160, which has a temperature of 60° C., at 1,050 kg/h to the further use (e.g. as fuel). The gas phase 170 obtained in the cyclone 2 with a temperature of 250° C. is cooled in two condensers 4 and 5 successively to initially 150° C. (4) and finally 50° C. (5). The liquid phases 180 and 181 obtained in each case, which comprise the monomeric isocyanate (TDI) and, where appropriate, solvent, are combined and passed into the condensate collection tank 6. The stream 190 which has not been condensed in 4 and 5 is divided: A part stream 191 is passed through a further condenser 9 and cooled to 30° C. there, and the liquid phase 183 obtained in this way is likewise fed to the condensate collection tank 6. The gas phase of the condensate collection tank is in contact with 190 via line 194. Non-condensable contents 195 are discharged from the process as a purge stream. After passing through the circulating gas fan 7 and enrichment with nitrogen 150, the part stream 192 is heated up to the required reactor entry temperature in the circulating gas heater 8 in order to provide the carrier gas stream 110 in this way. The valuable product, stream 200 (950 kg/h), is composed of the part streams 181 to 183. Depending on the precise configuration of the process, stream 200 still comprises contents of solvent, in addition to the monomeric isocyanate (TDI). Depending on the planned use, this is separated off by known processes. Preferably, however, stream 200 is added directly to the distillate of monomeric isocyanate obtained in step b) and worked up further together with this.

What is claims is:

1. A process for the preparation of an isocyanate, comprising:
    a) phosgenating of a primary amine to obtain a crude process product comprising the corresponding isocyanate,
    b) working up of the crude process product obtained under a), wherein the working up comprises at least one distillation step in which monomeric isocyanate, as the distillate, and a distillation residue comprising monomeric isocyanate are obtained,
    c) working up of the distillation residue obtained under b) by spraying the distillation residue and a carrier gas into a reactor, the distillation residue and the carrier gas flowing vertically downwards, so that the monomeric isocyanate vaporizes partly to completely and a dried residue which has been largely to completely freed from monomeric isocyanate and a stream comprising monomeric isocyanate are obtained.

2. The process according to claim 1, comprising removing the stream comprising the monomeric isocyanate in a lateral take-off of the reactor and removing the residue from the reactor below this lateral take-off.

3. The process according to claim 1, in which the temperature of the distillation residue when sprayed into the reactor is from 20° C. to 300° C. and the temperature of the carrier gas when sprayed into the reactor is from 150° C. to 500° C.

4. The process according to claim 1, in which the distillation residue is sprayed into the reactor under an absolute pressure of from 1.0 bar to 300 bar by means of a pressure nozzle.

5. The process according to claim 1, further comprising spraying a release agent selected from the group consisting of talc, chalk, inorganic pigments and completely polymerized residue is into the reactor.

6. The process according to claim 2, in which a fluidized bed of a fluidizing gas fed from the bottom and solid particles is established in the reactor below the lateral take-off for the stream comprising the monomeric isocyanate.

7. The process according to claim 1, in which the distillation residue (in step b) is obtained by concentration of the bottom product of a distillation step in a thin film evaporator, climbing film evaporator, failing film evaporator, long tube evaporator, helical tube evaporator, forced circulation flash evaporator or paddle drier or in a combination of these apparatuses, to obtain a gas phase comprising monomeric isocyanate and the distillation residue, as a liquid phase.

8. The process according to claim 1, in which the isocyanate is selected from the group consisting of toluylene-diisocyanate, diphenylmethane-diisocyanate, 1,6-hexamethylene-diisocyanate, isophorone-diisocyanate and diisocyanatodicyclohexylmethane.

9. The process according to claim 8, in which the isocyanate is toluylene-diisocyanate.

* * * * *